United States Patent [19]

Wagner et al.

[11] 4,197,836
[45] Apr. 15, 1980

[54] NUCLEAR CARDIAC BLOOD VOLUME DETECTING APPARATUS

[75] Inventors: Henry N. Wagner, Baltimore, Md.; Robert H. Wake, Warrensville Heights, Ohio

[73] Assignee: Bios Inc., Valhalla, N.Y.

[21] Appl. No.: 872,069

[22] Filed: Jan. 25, 1978

Related U.S. Application Data

[63] Continuation of Ser. No. 629,521, Nov. 6, 1975, abandoned.

[51] Int. Cl.² .............................................. A61B 6/00
[52] U.S. Cl. ................................. 128/654; 250/363 S; 128/659; 128/713
[58] Field of Search ............. 128/2 A, 2.05 F, 2.05 V; 250/363 S

[56] References Cited

U.S. PATENT DOCUMENTS

| | | | |
|---|---|---|---|
| 3,221,731 | 12/1965 | Annis et al. | 128/2 A X |
| 3,528,407 | 9/1970 | Vigoulet | 128/2.05 F |
| 3,777,142 | 12/1973 | Grenier et al. | 250/363 S |
| 3,860,822 | 1/1975 | Owens, Jr. | 250/363 S |

OTHER PUBLICATIONS

Hoffmann, G. et al., Nuclear-Medizin, 7, 1968, pp. 350-370.

Primary Examiner—Kyle L. Howell
Attorney, Agent, or Firm—McAulay, Fields, Fisher & Goldstein

[57] ABSTRACT

A built up image illustrating blood volume in the heart versus time taken over many cardiac cycles is produced by continuously displaying a graph of cumulative data indicating the amount of radioactivity from a tracer in the blood detected in the heart during each of a series of intervals into which the average cardiac period is divided. The parallel lines of a raster scan display correspond respectively to the memory channels. The count stored in a particular memory channel causes the video signal for the corresponding line to be maintained at a binary level for a corresponding time interval thus generating a bar graph in which the length of each bar indicates the amount of radioactivity sensed during the corresponding interval of the cardiac cycle. As each memory channel accumulates radioactivity data with each successive cardiac cycle, each bar displayed in the bar graph lengthens to indicate the cumulative activity until an interpretable curve is obtained.

13 Claims, 2 Drawing Figures

NUCLEAR CARDIAC BLOOD VOLUME DETECTING APPARATUS

This is a continuation, of application Ser. No. 629,521, filed Nov. 6, 1975, now abandoned.

BACKGROUND OF THE INVENTION

The invention relates generally to the field of nuclear medicine and, more specifically, to diagnostic techniques of analyzing blood flow through the heart by detecting radioactivity from radioisotopes injected into the bloodstream.

In addition to the standard tools of cardiac diagnosis, the electrocardiogram (ECG) and the conventional stethoscope for audible heart sounds, relatively new techniques including angiograms, ultrasound cardiography and the measurement of radioactivity in the blood are being investigated and implemented to increase the amount of quantitative data to provide a more reliable basis for diagnosis. In ascertaining the efficiency of the heart, it is desirable to determine the volumetric rate of flow of blood through the heart. For example, the difference in volume of the left ventricle during different phases of the cardiac cycle is indicative of the rate of blood flow.

Volumetric measurements can be approximated by using X-ray or ultrasound imaging techniques. Another type of X-ray technique is shown in U.S. Pat. No. 3,824,399 to Bjork et al which indicates the concentration of an X-ray opaque tracer in the heart over a period of several cardiac cycles to generate quantitative data concerning the rate of blood flow. The same type of technique was earlier employed by injecting a radioisotope into the blood stream entering the heart and using a scintillation detector or Geiger counter to determine the variations in concentration of the radioactive tracer in the outflow tract of the heart over several cardiac cycles. The collected data was plotted and used to determine the rate of blood flow through the heart. See, for example, U.S. Pat. Nos. 3,221,731 and 3,528,407 to Vigoulet et al.

SUMMARY OF THE INVENTION

The general purpose of the present invention is to generate a readily interpretable display of radiation (or gamma radiation) emitted from the heart blood pool at precise points in the cardiac cycle with the data for each point accumulated over many heart beats and displayed in one composite image showing the integrated activity at points within the cardiac cycle. A collimated probe aimed at a selected location in the heart detects the concentration of radioactive isotope in the blood by producing output pulses which are counted and stored over a brief repeating interval of time in a multichannel memory. A first channel of memory is gated by detection of the QRS complex in the patient's ECG. Thereafter, the channels of memory are successively addressed so that each successive radiation count over repeating time intervals will be stored in a corresponding memory channel. With the subsequent heart beat, the process is reiterated and a new count is added to the count that is already in storage for a particular channel.

Simultaneously, the memory channels are read out to a TV type display in which each memory channel is correlated with a "horizontal" line sweep. At the beginning of each line, the video input signal is switched from a low level to a high level where it remains for a period of time which corresponds to the accumulated total in the memory channels thus writing a line on the TV screen whose length is determined by the accumulated radioactivity counts.

Since successive lines of the display correspond to different points of the cardiac cycle, the physician can observe the build-up of an image over a period of about a minute which will illustrate the variation in concentration of radioactive isotope at that selected part of the heart blood pool during the patient's cardiac cycle. The same instrument is designed to operate in a "dynamic" mode, instead of being synchronized to the ECG, in which a nonreiterated (one-pass) test is performed by accumulating a radioactivity count over a longer period of time (e.g., 100 milliseconds) at each channel before the memory input is switched to the next channel.

DESCRIPTION OF THE PREFERRED EMBODIMENT

Figure 1:
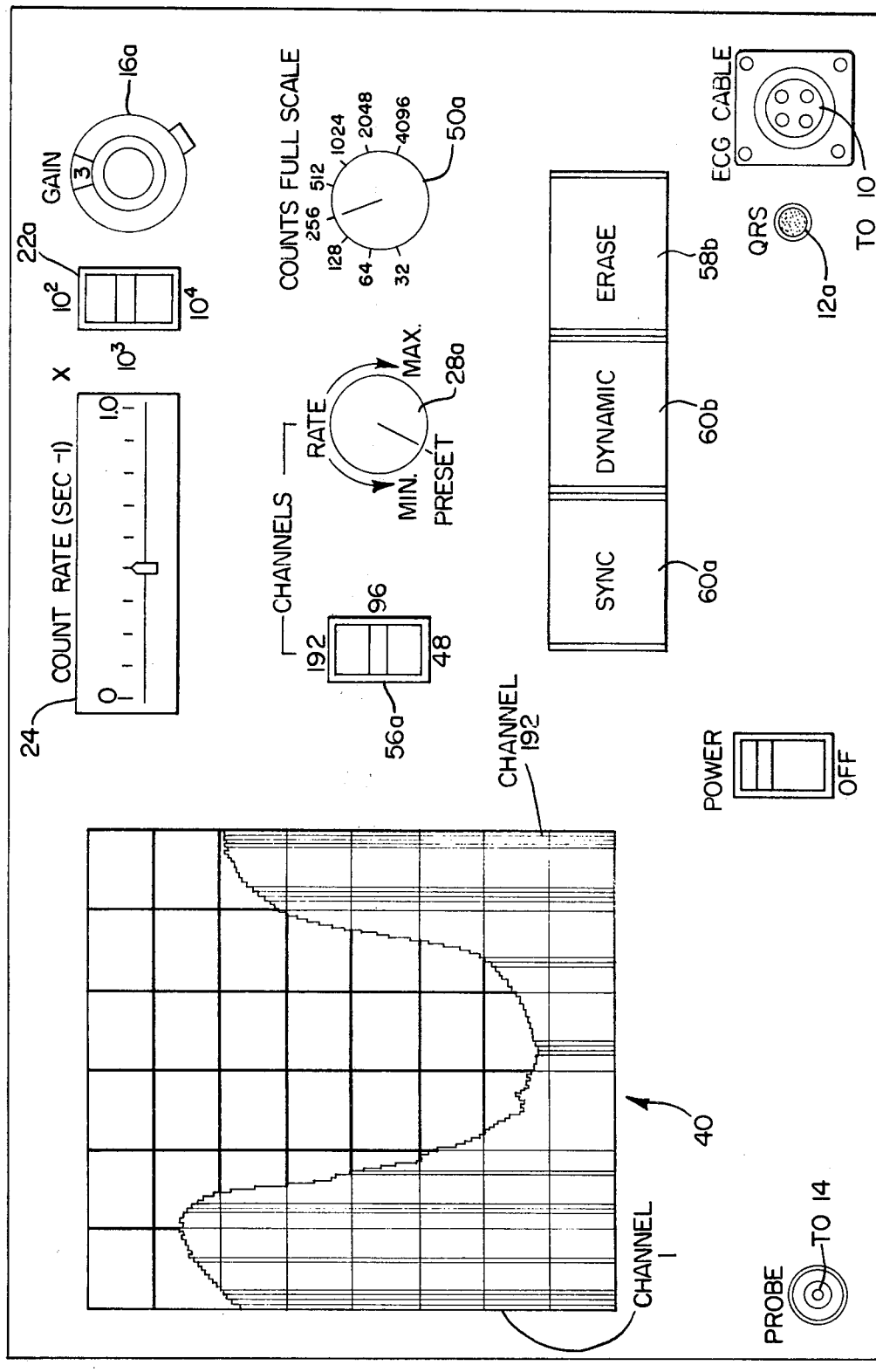
FIG. 1 is a front view of an instrument including a control panel and display screen with a pictorial representation of a typical image produced according to the present invention.

The instrument illustrated in FIGS. 1 and 2 and described below is designed to permit immediate visualization of the time-activity curve of a radioactive isotope carried in the blood within the patient's heart. The instrument has two modes of operation termed the "SYNC" and "DYNAMIC" modes. The block diagram in FIG. 2 illustrates all of the functional elements of the electronic system for operating in either mode.

The term SYNC mode is used because the storage of information is synchronized to the patient's ECG R-wave (center peak of the QRS complex). The storage interval for each memory channel as explained below is made short enough that a desired number of intervals can be sampled during each cardiac cycle. The synchronization aspect is manifested by the fact that the counter, which increments the channel destination or address for incoming data, is reset with each R-wave to "recycle" the memory channels. The SYNC mode can continue indefinitely until switched OFF, although it is effectively finished (and worthless for displaying) when all of the channels have been written completely full so that the memory is no longer registering new data.

In contrast, the DYNAMIC mode makes only a single pass through all of the memory channels with each channel being "open" for a much longer interval than in the SYNC mode. After the radioactivity in the final interval (last channel) has been counted, the DYNAMIC mode is automatically terminated.

The following detailed discussion will begin with a treatment of the system in the SYNC mode leaving certain control aspects to be explained at the end, such as how the DYNAMIC and SYNC modes are selected and initiated.

In FIG. 2 the patient's ECG signal is amplified and filtered to reject respiration, myogram, and other noise in the ECG isolation amplifier 10 and the QRS complex is discriminated by a conventional QRS detected 12 with front panel indicator light 12a (FIG. 1) to provide a reset signal for the memory channel switching system described below. A collimated probe 14, powered by an adjustable high voltage DC power supply 16 (typically 300–1000 volts DC), consists of a NaI crystal (typically 1½ inches in diameter), a photomultiplier tube and a shielded, deep-focus collimator with two irises, which yield an "icepick" or pinhole field of view. A gamma ray from the focal point of the probe 14, manually positioned in the heart blood pool, causes a current pulse from the probe 14 which is passed via a nuclear pulse amplifier 18 to a single channel analyzer 20. The analyzer 20 produces a digital output pulse signifying the receipt of a valid gamma ray, as evidenced by the output of the amplifier being between certain voltage limits. Note that the term "single channel" refers only to the fact that one kind of radiation is being detected and has nothing to do with the term multichannel memory used to designate the plurality of memory channels corresponding to adjacent intervals in the cardiac cycle.

A variable range ratemeter circuit 22 converts the pulse rate from the analyzer 20 to a voltage which drives the count ratemeter 24 to indicate whether the power supply 16 must be adjusted with knob 16a (FIG. 1), controlling the photomultiplier gain, to accommodate the particular isotope being used. The front panel switch 22a (FIG. 1) changes the range of the count ratemeter 22 by a factor of 100, 1000, or 10,000.

The digital pulse output of the analyzer 20 is simultaneously passed to the counter 26 which counts one "nuclear event" each time it receives a pulse from the output of the analyzer 20. In order to count the number of events in adjacent intervals within the span of a single cardiac cycle, the nuclear event counter is reset to zero (cleared) at the beginning of each interval by means of an adjustable time-per-channel time base generator 28. In the preferred embodiment, three options are available for the number of channels of memory: 192, 96 or 48, as discussed below. The time base generator 28, in cooperation with a frequency divider 29 (including multipliers if necessary), issues a clock pulse nominally every 5.12 milliseconds, 10.24 milliseconds or 20.48 milliseconds, as a function of the number of channels selected to provide coverage of the entire cardiac cycle at the approximate heart rate of 60 beats per minute. The nominal setting can be varied over a 4:1 range centered on the nominal setting via the front panel max./min. rate control knob 28a to accommodate the patient's heart rate, that is, to insure that all 192 channels, for instance, are being used.

The output of the nuclear event counter 26 is passed to a multichannel cumulative memory unit 30 including a two-input digital adder 32 and an addressable read/write memory 34 with nondestructive readout having 192 channels with 12 bits of storage per channel. The type of memory selected should be one which is capable of simultaneous write-in and readout of data, for example, a core storage matrix. The nuclear event counter 26 provides one of the inputs (A) to the adder 32. The other input (B) is provided by the data output of the memory 34. The output of the adder 32 forms the data input to the memory 34.

The memory is addressed by means of an input channel counter 36 which is reset (i.e., restarted) by the output of the QRS detector 12 via a mode switch 38 and clocked (incremented or decremented) by the time base generator 28. During each counting interval (e.g., 5.12 milliseconds) the memory 34 will be storing new cumulative data in a corresponding channel. In the next time interval, the input channel counter 36 readdresses the memory 34 to a corresponding memory channel. The memory 34 is thus operated in a cumulative fashion by combining the count for a particular interval with the count already stored in the corresponding channel of the memory for all prior corresponding intervals since starting the SYNC mode.

For the storage (input) operation, the address for the memory data output which is fed around to the digital adder 32 is controlled by the input channel counter 36 in the same manner as the input address is controlled.

In operation, the memory may be addressed by the input channel counter 36 very briefly once per time interval. For example, at the end of a given time interval, the memory address control is switched from the video section (explained below) to the input channel counter 36 so that the corresponding memory channel is held open for a brief interval of time during which the adder 32 is clocked just before the reset pulse from the time-per-channel time base generator 28 enabling the adder to sum the prior number in the memory channel at the output register and the count for the current interval and pass the summed count back into the same memory channel. After completion of the updating operation, control of the memory address is switched back to the video display system.

The video section of the instrument serves to display the updated contents of the memory channels all at once. The memory channels are visually represented by the display in the form of contiguous parallel lines with the number in each channel being represented by the length of a bar drawn on the line like the construction of a bar graph. Since the channels represent adjacent intervals of time, the display can be represented by an X-Y display where the X-axis represents time and the Y-axis represents radioactivity. The full extent of the X-axis corresponds to a single cardiac cycle and the displayed data represents the variation in radioactivity within the cardiac cycle. As the image is built up over a number of cardiac cycles, the displayed data tends to represent the variation in radioactivity within a typical or average cardiac cycle.

Figure 2:
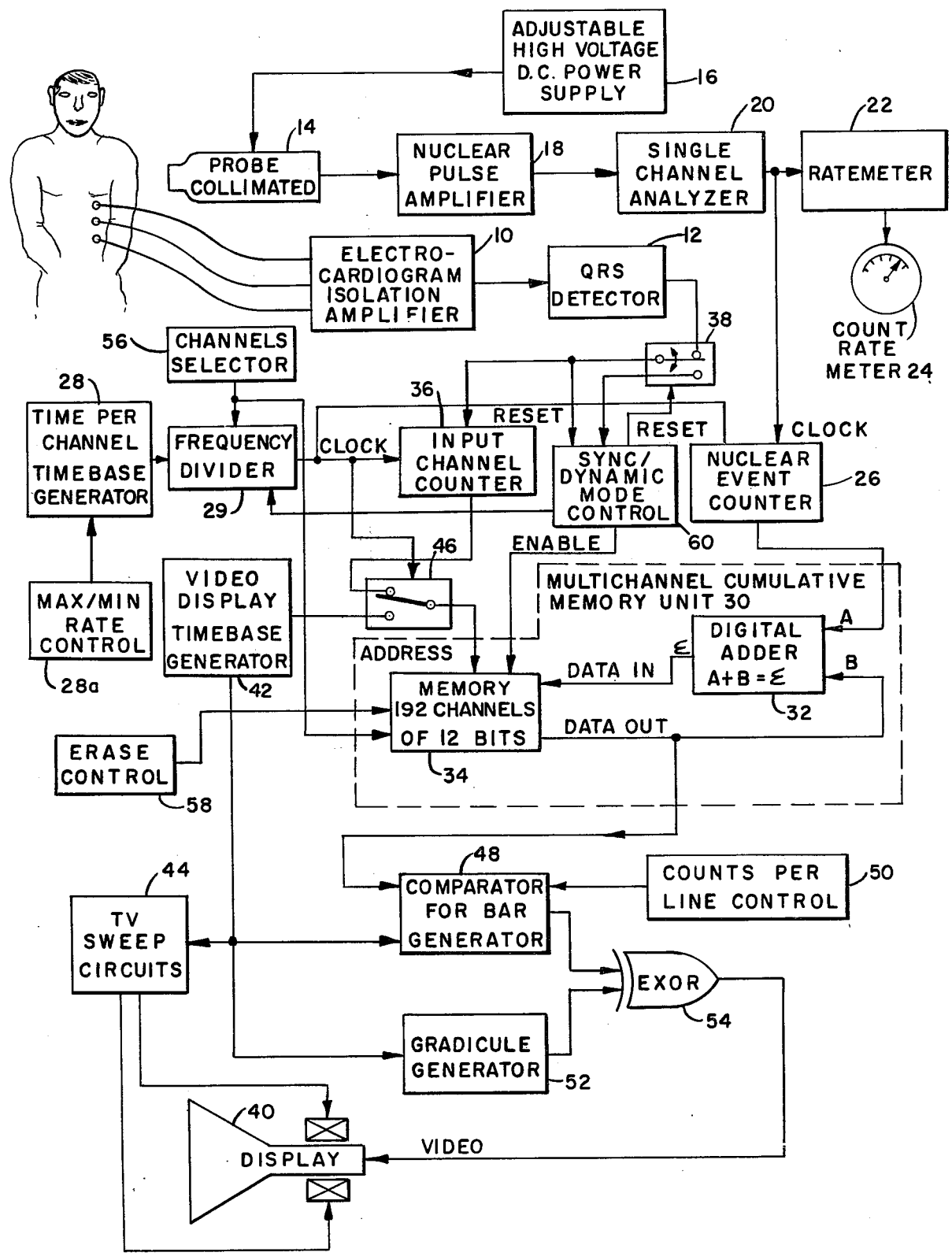
FIG. 2 is a block diagram illustrating the electronics associated with the instrument of FIG. 1.

The heart of the video section of the instrument is a conventional cathode ray (CRT) tube display 40 shown schematically in FIG. 2 and in front screen view of FIG. 1. A video display time base generator 42 provides appropriately timed SYNC pulses to the TV sweep circuits 44 such that horizontal and vertical deflection control signals are generated to produce a conventional raster scan pattern of the electron beam on the display 40. The raster pattern is oriented orthogonally relative to a conventional TV raster scan. That is, the lines run vertically. This is accomplished by rotating the TV monitor by 90°. The number of lines in the raster pattern can be determined roughly on a 1:1 relationship with the highest number of memory channels desired. However, there is no reason why the standard composite TV SYNC signal arrangement cannot be used, in which case 525 lines would be produced. If this number of lines were far greater than the number of channels employed, one channel would have to be represented by several adjacent lines to maintain suitable image size.

Besides controlling the generation of the raster pattern on the display 40, the video time base generator 42 also controls the readout function of the multichannel memory 34 at all times except those times at the end of one of the counting time intervals when the memory is updated with new cumulative data. The multiplexing of the address control is accomplished by means of a fast electronic switch 46 which is operated by the time-per-channel time base generator 28. At only one time during each counting time interval is the address controlled by the input channel counter 36. During this subinterval of time, the "update period," the corresponding memory channel is non-destructively interrogated along with the count of the nuclear event counter 26 and the two data are added together and run back into the corresponding memory channel. Outside the update period, the digital adder 32, i.e., the data input to the memory 34, is disabled. Following the update period, control of the address of the memory output is returned by means of the switch 46 to the video time base generator 42. The update period is designed to be so brief that it does not interfere with the display of the stored information.

The video time base generator 42 causes the output channel address of the memory 34 to be incremented or decremented at the same rate as the line SYNC signals so that each channel's contents will appear at the output simultaneously with each SYNC pulse which starts a line sweep deflection signal. The output register of the memory 34 is connected to one input of a comparator 48. The other input is interconnected with the video time base generator 42. The output of the comparator 48 produces the data video signal which causes a bar to be drawn on the corresponding line of the display with a length that is proportional to the number stored in the corresponding memory channel.

The comparator 48 can be implemented with digital or analog circuitry (not shown). The digital implementation requires a fast clock, which is ordinarily available in the form of the time base from which the video time base SYNC signals are generated. The fast clock operates a counter which is triggered or enabled by a line SYNC pulse. A standard digital comparator circuit receives in parallel the outputs of the memory channel and the continually incrementing output of the counter operated by the fast clock. When the count reaches the same number as in the input register for the memory 34, the digital comparator switches from one binary level to the other binary level.

Exactly the same comparing operation can be done in analog version by using a ramp generator triggered by a line SYNC pulse. The output of the ramp generator would form one input to a differential amplifier, or other comparing circuit, and the other input would be the output of a digital-to-analog converter connected to the memory output register. Both the digital and the analog implementation of the comparator 48 are considered to be strictly conventional for the stated function.

The digital output of the comparator 48 is thus synchronized with the lines of display 40. The data level of the video output (i.e., full white) is ON from the beginning of the line up to the point where the comparator 48 finds agreement between the memory channel contents and the reference ramp or count.

The highest useful number that can be contained in a given channel is deemed to be that indicated by a "1" in all 12 bits, which is equivalent in decimal number form to 4,095. The steepness of the analog ramp or the rate of the digital reference count used by the comparator 48 should be adjusted so that a full count (4,095) does not exceed the full "width" of the screen. However, since only a portion of the memory capacity may be used in a given test, it may be necessary to scale the count upward. This is accomplished by the counts per line control 50 in FIG. 2 which is operated by the calibrated "counts full scale" knob 50a on the front panel in FIG. 1. One way that this scaling up of the data can be accomplished is to take the binary number in the output register of the memory 34 and shift it one or more "more significant digits" (like moving the decimal point), before entering the number into the comparator 48. This type of operation is suggested by the powers of 2 calibrations on the counts full scale knob 50a in FIG. 1.

A preferred feature of this instrument is a self-generated grid which allows quantitative measurements of the variation in radioactivity to be measured without regard to non-linearity distortion. For this purpose, a gradicule generator 52 is operated by the same video time base generator 42 which operates the TV sweep circuits. The gradicule generator simply consists of clocked logic circuitry which writes equally spaced white dots along each line sweep to create vertical lines and a full line "white" every nth line to make the horizontal lines of the grid pattern. The video output of the gradicule generator 52 is passed along with the output of the comparator 48 to an EXCLUSIVE OR gate 54 which normally passes whichever one of the video outputs is "white." However, when both of the video outputs are white, the EXCLUSIVE OR gate is inhibited. The effect of this logical operation is to cause the lines of the grid to show up as black lines where they would run through the solid portion of the radioactivity curve so that they will be visible at all times as either white lines against a black background or black lines against a white background.

In normal operation the number of channels corresponds on a 1:1 basis with the number of lines available for viewing in the display. If desired, however, the number of channels may be selectively reduced. In the preferred embodiment, a channel number selector 56 operated by the three-position switch 56a on the front panel of FIG. 1 can be used to divide the number of channels by either 2 or 4 resulting in either 96 or 48 channels, respectively. While none of the radioactivity will be "missed" or not counted when the number of channels is halved, the resolution of the instrument is reduced. If 96 channels is selected, for example, instead of the full 192, the channel number selector 56 simply cuts out 50% of the memory channels. One way in which this can be accomplished is by using a presettable down counter for the input channel counter 36 where the preset number in the full channel case will be 192 (in decimal form) while in the half channels case, the number will be preset to only 96. In either case when the channel count comes down to zero, the counter 36 stops until commanded by the next R-wave to start counting down again from the preset number. At the same time, the channel number selector 56 can be used via the frequency divider 29 to double or quadruple the time interval clocked by the time-per-channel time base generator 28. At the same time, the channel number selector 56 must also correct the comparator 48 which produces the video bars. Accordingly, each memory channel is interrogated for two lines or four lines so that two or four equal length-contiguous, parallel bars are written.

Another way to make the video display come out full screen even though the number of channels is divided by two or four would be to connect the memory channels in tandem or in groups of four depending on the setting of the channel number selector 56. For the first address, for example 96, the same data will be entered into two adjacent channels which would normally correspond, for example, to channels 192 and 191. In this way, the video display can read out the channels at the same rate as if the full channel capacity of the memory were being used.

The remaining functions provided on the front panel of the instrument are "SYNC," "DYNAMIC," and "ERASE." The erase control 58 (FIG. 2) operates in a conventional manner to clear the entire memory on command by resetting all 2,304 bits to zero.

The SYNC/DYNAMIC mode control unit 60, operated by means of the SYNC and DYNAMIC push buttons 60a and 60b on the front panel, has several functions. If the SYNC mode is desired, pushing the SYNC button (e.g., a bistable electro mechanical switch) causes the storage operation to begin with the next R-wave from the patient. Thus, the mode control 60 could be implemented by means of a gated flip-flop where the data input is represented by the position of the SYNC switch and the output of the QRS detector 12 is the clock pulse which sets the output of the flip-flop to enable the memory to receive data. Thus, once the SYNC switch is set, the SYNC mode of operation will continue indefinitely until the memory capacity is exhausted or until the SYNC switch is repositioned whereupon the SYNC mode will terminate on the next R-wave. The display will continue to be built up, if permitted, until the entire screen is white.

If the DYNAMIC (single-pass) mode of operation is desired, the patient's R-wave is of no interest. Thus, throwing the DYNAMIC switch 60b causes the mode switch 38 to open the connection between QRS detector 12 and the reset (preset enable) input of the channel counter 36. Instead of being initiated by the patient's R-wave, the channel counter 36 is reset by actuation of the DYNAMIC switch. In addition, selecting the DYNAMIC mode of operation instantaneously enables the memory 34 and via the frequency divider 29 (or equivalent circuitry) changes the counting interval timed by the channel time base generator 28 to a much longer interval on the order of 100 milliseconds instead of 5.12 milliseconds. One hundred ninety-two 100 millisecond intervals results in a 19.2 second study which is automatically terminated by virtue of the fact that the channel counter 36 is not reset after it counts 192 channels.

In use, the portable instrument is brought to the bedside and the patient is typically prepared by injecting albumin containing a radioactive isotope, for example up to 30 millicuries of technetium-99m, directly into the bloodstream entering the heart and the connections for the ECG unit are made. About ten minutes after injection of the tracer, the physician holds the probe 14 (FIG. 2) over the patient's precordium and, observing the count ratemeter, locates the focal point in the heart blood pool (e.g., the left ventricle). Once the probe is located, the SYNC button is actuated and the image observed for about a minute until an interpretable curve is obtained.

If during image build-up, the physician feels that a change in the number of channels is in order, the instrument is taken out of SYNC mode, the memory erased, adjustments made and the SYNC mode restarted. The SYNC mode can be interrupted and restarted, if desired, without erasure.

The above detailed description is not intended to restrict the invention as claimed below to any particular form where equivalent implementations exist to carry out the recited function. For example, the collimated probe 14 and nuclear pulse amplifier 18 represent only one way of detecting or sensing radioactivity from a particular point in the heart blood pool and any other available technique for detecting radiation may be substituted. Moreover, other X-Y display techniques can be substituted for the TV video display of the preferred embodiment. Rather, the description is intended to be merely illustrative of a preferred embodiment of the invention designed to meet certain criteria and specifications which to some degree depend on the specific application and environment in which the instrument will be used. Accordingly, all variations within the range of equivalence are intended to be embraced by the claims which follow.

What is claimed is:

1. A system for displaying the variation in radioactivity within a patient's cardiac cycle from a tracer substance in the blood comprising: detector means for providing an output indicative of the amount of radiation emitted from a selected location in the heart blood pool; timing means for determining successive sampling intervals; nuclear event integrator means responsive to said timing means and said detector means output for producing an output indicative of the amount of said radiation detected in each successive sampling interval; addressable N channel cumulative memory means for accumulating a representation of the total amount of radiation indicated by said integrator means for every nth sampling interval in a corresponding one of N memory channels; heart beat responsive means for generating a synchronizing pulse at the patient's heart rate; memory channel addressing means responsive to said timing means and said heart beat responsive means for incrementing the input channel address for said memory means with each sampling interval in a repeating sequence of N predetermined channel addresses in which each successive sequence is initiated by said synchronizing digital pulse; and means for displaying simultaneously the contents of all N channels of said memory means in the format of N adjacently spaced visible indicia each having a height above a common axis according to the current cumulative total represented in the corresponding memory channels respectively.

2. The system of claim 1 wherein said displaying means includes means for producing said visible indicia in the form of N adjacent parallel lines each having lengths corresponding to the cumulative total represented in the corresponding memory channels respectively.

3. The system of claim 1, wherein said detector means includes transducer means for producing output pulses indicative of radiation emitted from a selected location in the heart blood pool and analyzer means responsive to the output pulses of said transducer means for producing a digital pulse output indicative of a particular kind of radiation; and said integrator means includes a nuclear event counter means for counting the number of digital pulses in each successive sampling interval.

4. The system of claim 1, wherein said memory means includes an N channel addressable read/write digital memory and two-input adder means having one input connected to the memory readout and the other input connected to the nuclear event integrator means for producing the sum of the two inputs as the data input to said memory for providing a cumulative total in said memory of the output of said nuclear event integrator means.

5. The system of claim 1, wherein said displaying means includes a video display, means for generating a raster scan in said display comprising a sequence of at least N adjacent line sweeps, and comparator means synchronized with said raster scan for generating a digital data video signal beginning approximately at the start of each line sweep and terminating during the line sweep after an interval corresponding to the cumulative total in the corresponding memory channel of said memory means to produce a composite data image on said video display.

6. The system of claim 5, wherein said comparator means includes means for interrogating the channels of said memory means at the rate of said raster scan.

7. The system of claim 5, wherein said displaying means further includes means for generating a digital gradicule video signal to produce a grid pattern of lines on said display, and EXCLUSIVE OR means for gating said data and gradicule video signals to said display such that coincidence of the two signals results in reduced video signal so that the grid pattern is not obscured by said data image.

8. The system of claim 1, further comprising means for adjusting said sampling interval over a predetermined range to allot N consecutive sampling intervals to the patient's cardiac period.

9. The system of claim 1, further comprising means for selectively dividing the number of memory channels in said memory means and correspondingly lengthening the sampling interval to lower the resolution of the display.

10. The system of claim 1, further comprising means for disconnecting said memory channel addressing means from said synchronizing pulse and for sequencing said memory means once through said N channels on command.

11. A system for displaying the variation in radioactivity within a patient's cardiac cycle from a tracer substance in the blood comprising:
    detector means for providing an output indication of the amount of radiation emitted from a selected location in the heart blood pool; timing means for determining a sampling interval; means for producing an output indicative of the cumulative amount of the radiation in each corresponding sampling interval over a number of cardiac cycles.

12. The system of claim 11, further comprising means for synchronizing said sampling intervals with the patients cardiac cycle.

13. The system of claim 11, further comprising means responsive to said producing means for displaying a graphical feature for each interval, which for a given interval is indicative of the current sum or previous outputs said detector means during said given interval.

* * * * *